United States Patent [19]

Weinstein et al.

[11] Patent Number: 4,753,958

[45] Date of Patent: Jun. 28, 1988

[54] PHOTOCHEMOTHERAPY OF EPITHELIAL DISEASES WITH DERIVATIVES OF HEMATOPORPHYRINS

[75] Inventors: Gerald D. Weinstein; Jerry L. McCullough, both of Irvine, Calif.

[73] Assignee: University of CAL Berkeley, Berkeley, Calif.

[21] Appl. No.: 878,308

[22] Filed: Jun. 25, 1986

Related U.S. Application Data

[63] Continuation-in-part of Ser. No. 699,484, Feb. 7, 1985, abandoned, which is a continuation of Ser. No. 384,537, Jun. 3, 1982, abandoned.

[51] Int. Cl.$^4$ ............................................. A61K 31/40
[52] U.S. Cl. .................................... 514/410; 514/422; 514/863
[58] Field of Search ................ 514/422, 427, 410, 863

[56] References Cited

U.S. PATENT DOCUMENTS 2,858,320 10/1958 Woods et al. ................... 260/245.91
4,235,887 11/1980 Vorhees et al. ...................... 424/180
4,424,210 1/1984 Rajadhyaksha ...................... 424/180

OTHER PUBLICATIONS

Diezel et al. (1980 Dermatol Monatsschr. 166 793–797).
Chemical Abstracts 83:141830w (1975).
Chemical Abstracts 85:58859h (1976).
Weinstein et al. (1981) Arch. Derm. 117:388–393.
Rettenmaier et al., *Gynecologic Uses of Photoradiation Therapy* (Clayton Symposium, Santa Barbara, Calif. 9183).
McCullough et al. (1983) ICALEO 37:4–7.
Silver (1937) Archives of Dermatology and Syphilology 36:1118–1119.
Diezel et al. (1981) Dermatol. Monatsschr. 167:44.
Diezel et al. (1983) Studia. Biophys. 94:45–46.
McCullough et al. (1983) J. Invest. Dekm. 81:528–532.
Berns et al. (1984) Lasers in Surgery and Medicine 4:73–77.
Dermatology Times, p. 17 (Mar. 1984).
Goldman et al., "Investigative PRI Therapy: (Abstract), Porphyrin Photosensitization Workshop (Wayne St. Univ. Jul. 6–7, 1984.
Lipson et al. (1961) J. Thoracic and Cardiovas. Surg 42:623–629.
Lipson et al. (1964) Obstetrics and Gynecology 24:78–84.
Lipson et al. (1964) Diseases of the Chest 46:676–679.
Granelli et al. (1975) Cancer Res. 35:2567–2570.
Kelly et al. (1976) Urology 115:150–151.
Dougherty et al. in *Research Photobiology*, pp. 435–446, A Castellani ed 1977.
Dougherty et al. (1978) Cancer Res. 38:2628–2635.
Dougherty et al. (1979) J. Nat'l Canc. Ins. 62 231–237).
Cooper Medical, *Introduction to Photodynamic Therapy* (1982).
Dougherty et al. in *The Science of Photomedicine*, pp. 625–638 (J. D. Regan & J. A. Parrish eds, 1982).
Dougherty et al. in *Cancer Principles & Practice of Oncology*, pp. 1836–1844 (V. T. DeVita, Jr., S. Hillman & S. A. Rosenberg eds 1982).
*Oncology*, pp. 1836–1844 (V. T. DeVita Jr., S. Hillman & S. A. Rosenberg eds. 1982).
Moan et al. (1982) Cancer Lett. 15:161–166.
Dougherty et al. in *Porphyrin Photosensitization*, pp. 3–13 (D. Kessel & T. J. Dougherty eds. 1983).
Dougherty (1984) CRC Crit. Rev Oncology/Hermatology 2 83–116.
Dougherty et al. in *Porphyrin Localization and Treatment of Tumors*, pp. 301–314 (1984).
Lange et al. (1980) Dermatol. Monatsschr. 166:599–603.

*Primary Examiner*—Leonard Schenkman
*Attorney, Agent, or Firm*—Ciotti & Murashige, Irell & Manella

[57] ABSTRACT

Topical compositions for the treatment of an epithelial disease, such as psoriasis and cervical displasia, containing phototoxic derivatives of hematoporphyrin and methods for treating epithelial diseases with phototoxic derivatives of hematoporphyrin.

44 Claims, 1 Drawing Sheet

PHOTOCHEMOTHERAPY OF EPITHELIAL DISEASES WITH DERIVATIVES OF HEMATOPORPHYRINS

CROSS-REFERENCE TO RELATED APPLICATION

This application is a continuation-in-part of Ser. No. 699,484, filed Feb. 7, 1985, now abandoned, which is a continuation of Ser. No. 384,537, filed Jun. 3, 1982, now abandoned.

TECHNICAL FIELD

This invention relates to photochemotherapy of epithelial diseases, such as psoriasis and cervical displasia. This invention also relates to topical or intradermal application of certain derivatives of hematoporphyrin in the course of photochemotherapy for an epithelial disease.

BACKGROUND OF THE INVENTION

The invention described herein was made in the course of work under a grant or award from the U.S. Department of Health and Human Services.

Epithelial diseases (epidermal and mucosal) are a major health problem. Of particular concern are those characterized by abnormal (increased) rates of cell turnover, referred to herein as hyperproliferative epithelial diseases. Examples of hyperproliferative epithelial diseases include psoriasis, cutaneous tumors primary to the skin (basal cell carcinoma, squamous cell carcinoma, melanoma, mycosis fungoides. Bowen's disease), viruses (warts, herpes simplex, condyloma acuminata), premalignant and malignant diseases of the female genital tract (cervix, vagina, vulva) and premalignant and malignant diseases of mucosalf tissues (oral, bladder, rectal). The common diseases within this class are psoriasis and cervical displasia, psoriasis being the most common. Recent estimates have indicated that there are 1 to 3 million persons in the United States with psoriasis, and approximately 150,000 to 250,000 new cases reported annually. The prevalence rate of psoriasis in the United States is between 3% and 4% of the population, with similar prevalence rates in other countries. There is a great need, therefore, for an effective therapeutic regimen.

A variety of therapies are currently used to treat psoriasis including dialysis, chemotherapy (topical and systemic), and photochemotherapy (topical and systemic). Topical chemotherapy is probably the most widely used, employing agents such as tar, retinoids, anthralin, corticosteroids, and antimetabolites.

At present, the most severe cases of psoriasis are being treated with systemic photochemotherapy, which is potentially carcinogenic. Parrish et. al. (1970), *Biochem Biophys Acta* 217:30, describes the use of oral methoxysalen and long-wave ultraviolet light (PUVA) for the treatment of psoriasis. Clinically, PUVA has remained relatively effective for the majority of patients, while short-term side effects, such as widespread serve erythema, have been tolerable for the severely afflicted patient.

The proposed mechanism for the therapeutic action of PUVA is based on the binding of psoralens to the DNA of the afflicted cells. In this photochemical reaction, psoralen photoadducts with DNA-thymine bases are formed. Psoralan can also intercalate with two DNA base pairs and give intrastrand cross linkages. The inhibition of DNA synthesis and consequent blocking of cell division that results from this photochemical reaction of DNA and psoralen may be the therapeutic mechanism in the treatment of psoriasis.

While the inhibition of DNA synthesis may be the desirable outcome of psoriasis therapy, there is concern that the direct changes in the DNA structure and function by PUVA may have potential carcinogenic and mutagenic effects. It has been reported, for example, that there is an increased pattern of skin cancers developing in patients following PUVA. R.S. Stern et. al. (1979) *New England Journal of Medicine*, 300:809–813. Thus, while prior art methods of PUVA have shown some promise in the treatment of epithelial diseases, erythema over unafflicted areas of the patient and the potential carcinogenic effect of these treatments make it desirable to develop new therapeutic strategies equally or more effective which do not have potential for such undesirable side effects.

The first report in the literature of the treatment of psoriasis with hematoporphyrin appeared in 1937. The patient was treated systemically with hematoporphyrin and then exposed to ultraviolet light. H. Silver (1937) *Archives of Dermatology and Syphilology*, 36:1118–1119. Hematoporphyrin has also been reportedly used in photochemotherapy for glioma cells employing visible light. S. G. Granelli et. al., (1975) *Cancer Research*, 35:2567–2570.

In 1960, Hematoporphyrin Derivative (HPD) was introduced. It is a mixture of hematoporphyrins, such as hematoporphyrin, hydroxyethylvinyl deutero porphyrin, protoporphyrin, and dihematoporphyrin ether. There are probably other porphyrin derivatives included in HPD as well. See R. L. Lipson, *The Photodynamic and Fluorescent Properties of a Particular Hematoporphyrin Derivative and its Use in Tumor Detection* (Masters Thesis, University of Minnesota 1960); R. L. Lipson et al, (1961) *Journal of the National Cancer Institute* 26:1–8: T. J. Dougherty et al in *Porphyrin Localization and Treatment of Tumors*, pp 301–314 (1984). Hematoporphyrins, and in particular HPD, have been studied in recent years for their potential usefulness in both the diagnosis and treatment of malignant disease. The property of selected localization of hematoporphyrins, such as HPD, in animal and human malignant tissues has been exploited for the fluorescent delineation of solid tumors, while the photodynamic action of the compound has been utilized to destroy malignant tissues selectively.

Due to its ability to localize in malignant cells and fluoresce, HPD has been employed in diagnostic methods directed to the detection of malignant tissue. See R. L. Lipson (1960), supra; R. L. Lipson et al (1961), supra; R. L. Lipson et al (1961), *Journal of Thoracic and Cardiovascular Surgery* 42:623–629; R. L. Lipson et al (1964) *Diseases of the Chest* 46:676–679; R. L. Lipson et al (1964) *Obstetrics and Gynecology* 24:78–84; H. B. Gregorie, Jr. et al (1968) *Ann Surg* 167:827–829. In general, the above diagnostic protocols involve the systemic administration of HPD to the patient, followed by the irradiation of the suspect tissue, with either ultraviolet or visible light, to see if it fluoresces.

The therapeutic potential of HPD for tumors was demonstrated in 1972 when glioma tumors transplanted into rats were destroyed by the combined effect of HPD and visible light. I, Diamond et al (1972) *Lancet* 2:1175–1177. Since that time, several clinical trials using HPD photoirradiation therapy have been reported in patients with cutaneous or subcutaneous malignant tumors. See. e.g., T. J. Dougherty et al (1978) *Cancer Research* 38:2628–2635: T. J. Dougherty et al in *The Science of Photomedicine.* pp 625–638 (J. D. Regan & J. A. Parrish, eds., 1982): T. J. Dougherty et al in *Cancer, Principles and Practice of Oncology,* pp 1836–1844 (V. T. DeVita Jr., S. Hellman, & S. A. Rosenberg, eds. 1982).

The cytotoxicity induced by HPD appears to result from the intracellular formation of singlet oxygen (a short-lived, highly reactive state of the oxygen molecule) when cells containing the porphyrin are exposed to visible light. K.R. Weishaupt et al (1976) *Cancer Research* 36:2326–2329. While the exact nature of the cytotoxicity induced by the singlet oxygen pathways is not known, it does not appear to involve the structure and function of DNA directly. The plasma membrane appears to be the main target for cellular destruction in in vitro studies. T. J. Dougherty, "Clinical and Scientific Advances in Photoradiation Therapy" (Porphyrin Photosensitization Workshop, Washington, D.C., Sept. 1981). It has been reported that HPD and visible light cause extensive enzyme inactivation of mouse DNA-dependent RNA polymerase. B. Munson *Proc of AACR and ASCO,* p 256 (1979) (abstract). Exposure of template DNA to the identical conditions, however, does not cause significant changes in the viscosity or template activity for the RNA polymerases. It was concluded that inactivation of these polymerases is much more sensitive than changes in DNA by HPD-mediated photodynamic action. This suggests the possibility that inactivation of RNA polymerases may be critical in the toxicity to eucaryotic cells caused by this treatment.

Thus there are two possible mechanisms of action that have been found experimentally to be more likely than a DNA interaction, thereby greatly decreasing the change of carcinogenic or mutagenic side effects from therapies based upon HPD.

It has recently been determined that the compound which is active against malignant tissue in the mixture of porphyrins which comprise HPD is dihematoporphyrin ether (DHE). T.J. Dougherty et al, in *Porphyrin Localization and Treatment of Tumors,* pp 301–314 (1984); T. J. Dougherty (1984) *CRC Critical Reviews in Oncology/-Hematology* 2:83–116. It was determined in these studies that HPD enriched for DHE and administered systemically in a photochemotherapy protocol showed phototoxic properties toward malignant cells. DHE, however, is not the component of HPD responsible for the majority of fluorescence when HPD is used diagnostically. These studies do not report the activity of DHE against nonmalignant proliferative skin disease, or whether it is effective when applied topically or locally.

The above therapies based on hematoporphyrins all suffer from a single significant drawback: they require the systemic administration of the drug. Thus, the patient's entire skin is photosensitized. This whole-body photosensitivity after systemic injection requires that the patient avoid direct sunlight or prolonged contact with bright artificial light for several weeks. If the patient does not avoid contact with such light, widespread and severe erythema can result. Since many epithelial diseases only affect a small and superficial area, it seems unreasonable to treat such patients with a systemic medication and expose them to these side effects. One solution to this problem would be to develop a composition with a photoactive drug which is effective when applied topically. Topically applied drugs provide an ideal method of localizing the effects of the drug, since they need only be applied to the afflicted tissue. Many drugs which act systemically, however, are ineffective in topical formulations.

There is a clear need, therefore, to provide an effective treatment of hyperproliferative epithelial disease which avoids such serious side effects as carcinogenesis, mutagenesis and whole-body photosensitization.

SUMMARY OF THE INVENTION

It is an object of the present invention to provide an effective therapeutic method for the treatment of hyperproliferative epithelial diseases, such as psoriasis and cervical displasia.

It is also an object of the present invention to provide a topical or intradermal preparation for the treatment of hyperproliferative epithelial diseases.

Yet another object of the present invention is to provide an improved photochemotherapeutic method for the treatment of hyperproliferative epithelial diseases, as well as improved photochemotherapeutic agents.

Still another object of the present invention is to provide a method of treating hyperproliferative epithelial diseases with Hematoporphyrin Derivative, or its active components, which avoids the serious side effects associated with the systemic administration of such compounds.

These and other objects and advantages of the present invention will be readily apparent to those of skill in the art from the following embodiments.

The present invention resides in the discovery that HPD, and more specifically DHE, is an effective therapeutic agent when applied topically or intradermally to tissue afflicted by a hyperproliferative epithelial diseases, such as psoriasis or cervical displasia. The present invention is applicable to the treatment of hyperproliferative epithelial diseases in animals, such as mammals, and particularly in humans.

In one embodiment, the present invention is directed to a composition for topical application in the photochemotherapy of hyperproliferative epithelial diseases comprising a topical carrier and a therapeutically effective amount of the component of Hematoporphyrin Derivative that is phototoxic to psoriatic tissue (i.e., DHE).

In another embodiment, the present invention is directed to a composition for topical application in the photochemoterapy of hyperproliferative epithelial diseases comprising a topical carrier and a therapeutically effective amount of Hematoporphyrin Derivative.

A further embodiment of the present invention is directed to a method of photochemotherapy for hyperproliferative epithelial diseases comprising: (a) treating an area of tissue afflicted by a hyperproliferative epithelial disease by applying topically or intradermally a therapeutically effective amount of the component of Hematoporphyrin Derivative that is phototoxic to psoriatic tissue: and (b) exposing said treated area of skin to radiation that photoactivates said component of Hematoporphyrin Derivative to produce a cytotoxic response in said afflicted tissue.

DETAILED DESCRIPTION OF THE INVENTION

Figure 1:
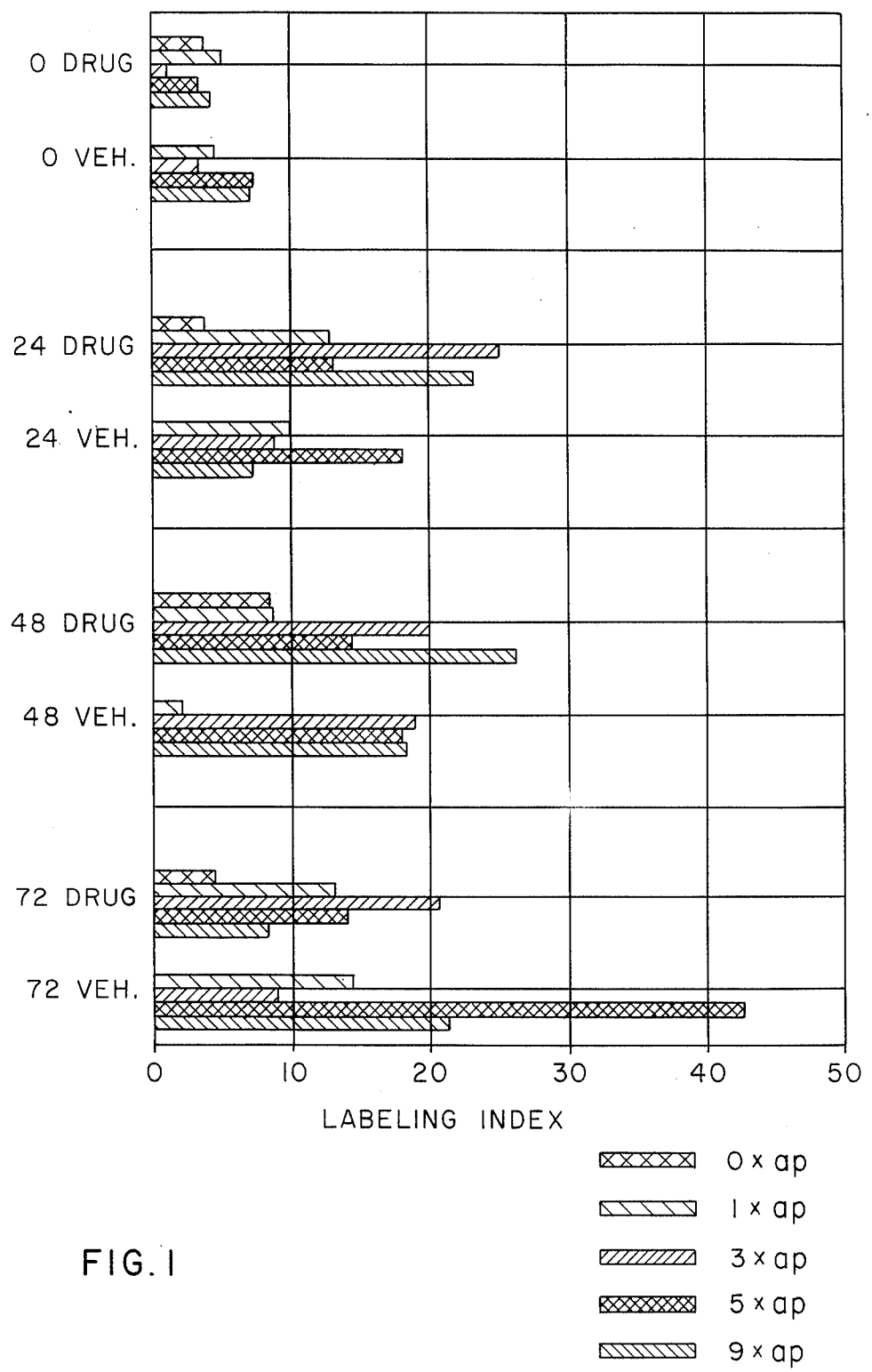
FIG. 1 presents data indicating the effect of topical DHE treatments upon epidermal DNA synthesis in vivo.

It has been surprisingly discovered that Hematoporphyrin Derivative (HPD), or the anti-psoriatic component thereof, dihematoporphyrin ether (DHE), can be used effectively in the photochemotherapy of hyperproliferative epithelial diseases in mammals such as humans, even though it is administered topically or intradermally. This avoids the problems associated with the prior art method of systemic administration of photoactive drugs. For example, systemic administration of such drugs requires that the patient stay out of sunlight or other bright lights for up to a month because the entire skin of a patient becomes sensitized from the drug, making the patient subject to severe erythema over the entire body. The present invention, by applying the phototoxic agent either topically or intradermally, confines the phototoxic drug to the afflicted tissue. The present invention also avoids the use of prior art drugs which could be carcinogenic or mutagenic. A further advantage of the present invention is that applicants have determined that HPD or DHE can be photoactivated effectively against hyperproliferative tissue without resort to some of the more damaging forms of radiation employed in the photoactivation of hematoporphyrins in cancer therapy. The present invention can be practiced without the use of UVB radiation which mutagenizes cells, or lasers which can burn tissue. Rather, the method of the present invention can be practiced with the relatively safe forms of radiation, such as the red portion of the visible spectrum or UVA.

The term "hyperproliferative epithelial disease", as used herein, means conditions of the skin that are characterized by epidermal cell proliferation or incomplete cell differentiation. These conditions may occur spontaneously or be induced by means external to the body, such as exposure to radiation or chemicals. Such diseases include psoriasis, cervical displasia and other premalignant lesions, and mycosis fungoides. The topical or intradermal compositions of the present invention may also be used to treat other hyperproliferative epithelial disease, including viral diseases such as herpes simplex and warts, cutaneous malignancies primary to the skin (e.g., squamous cell carcinoma, basal cell carcinoma, melanoma), and metastatic lesions of internal malignancies present on the skin. Additional examples of diseases which can respond to the treatments described herein include atopic dermatitis, vitiligo, nonspecific dermatitis, primary irritant contact dermatitis, allergic contact dermatitis, ichthyosis, epidermolytic hyperkeratosis, premalignant sun-induced keratosis, nonmalignant keratosis, actinic keratosis, and seborrheic dermatitis. Of particular concern to the present invention is the treatment of hyperproliferative epithelial diseases such as psoriasis and cervical displasia.

The term "phototoxic hematoporphyrin" is used herein to refer collectively to Hematoporphyrin Derivative, which is an art-recognized term for a mixture of porphyrins, as well as the active component thereof, DHE, or fractions of HPD enriched in DHE. HPD is prepared by acetylating hematoporphyrin with an acetic acid-sulfuric acid mixture followed by hydrolysis under basic or near-neutral conditions. R. L. Lipson, *The Photodynamic and Fluorescent Properties of a Particular Hematoporphyrin Derivative and Its Use in Tumor Detection* (Masters Thesis, University of Minnesota, 1960). Hematoporphyrin Derivative is available commercially from Photofrin Medical, Inc., Raritan, NJ, in a 5 mg/ml saline solution sold under the trade name Photofrin. A fraction of HPD enriched in the active component, DHE, can be produced by HPLC. *Porphyrin Localization in Treatment of Tumors*, pp. 301-314 (1984). This enriched fraction can also be purchased from Photofrin Medical, Inc., under the trade name Photofrin II.

Hyperproliferative epithelial disease is treated according to the present invention by administering a phototoxic hematoporphyrin to the afflicted tissue either topically or intradermally. The phototoxic hematoporphyrin is administered in a therapeutically effective amount. The determination of an appropriate dosage is well within the skill of the ordinary artisan, and will depend upon various factors, such as the particular disease, the stage of the disease, the condition of the skin, as well as others.

When local (intradermal) administration of the phototoxic hematoporphyrin is employed, it is typical to administer at least about 5 $\mu$g of HPD per $cm^2$ of afflicted skin, generally in the range of about 5 to about 500 $\mu g/cm^2$. Because of its higher activity, DHE can usually be administered at about one-half the level of HPD and retain the same efficacy. The phototoxic hematoporphyrin administered locally can be formulated with any pharmaceutically acceptable carrier, such as physiologic saline, and such formulations (as well as dosages) are within the skill of the art.

In topical application, the ultimate dosage delivered to the afflicted tissue will depend upon the concentration of the phototoxic hematoporphyrin in the topical carrier, the amount of the topical composition which is applied to the afflicted tissue, the number of times it is applied, the condition of the skin, as well as other factors. In general, concentrations of the phototoxic hematoporphyrin in the topical composition can range from about 0.1% to about 10% by weight, although concentrations outside of this range could be efficacious depending upon other factors. More typical concentrations will lie in the range from about 0.5% to about 5% by weight of the composition, preferably from about 0.5% to about 1.5%, and most preferably about 1% (all by weight of the total composition). As in the intradermal formulations, the higher efficacy of DHE will usually allow the amount of DHE employed to be about half that of the amount of HPD employed.

A major component of compositions for topical application will be a topical carrier. The term "topical carrier" as used herein refers to carrier materials suitable for topical applications of drugs, such as phototoxic hematoporphyrins, and include any such materials known in the cosmetic and medical arts. Suitable carriers include, for example, water, liquid alcohols, liquid glycols, liquid polyalkylene glycols, liquid esters, liquid amides, liquid protein hydrolysates, liquid alkylated protein hydrolysates, liquid lanolin and lanolin derivatives, and like materials commonly employed in cosmetic and medicinal compositions. Exemplary carriers herein include alcohols, including both monohydric and polyhydric alcohols, e.g., ethanol, isopropanol, glycerol, sorbitol, 2-methoxyethanol, diethylene glycol, ethylene glycol, hexylene glycol, mannitol, and propylene glycol; ethers such as diethyl or dipropyl ether; polyethylene glycols and methoxypolyoxyethylenes, carbowaxes having molecular weights ranging from 200 to 20,000, polyoxyethylene glycerols, polyoxyethylene, sorbitols, and stearoyl diacetin. Oil-in-water emulsions, such as cold cream bases, can also be used. The topical carriers described herein also include various agents and ingredients commonly employed in dermatological and cosmetic ointments and lotions. For example, perfumes, thickening agents such as carboxymethylcellulose, stabilizers, surfactants, emolients, coloring agents, and the like also can be present in the carrier.

Topical carriers, such as ointments, creams, salves, jellies, pastes and lotions, are collectively referred to herein as "viscous topical medicament carriers." In general, viscous topical medicament carriers are a lubricating or moisturizing type which do not dry the patient's skin, as do carriers comprised primarily of water and alcohol. An example of a viscous topical medicament carrier is Eucerin TM cream, available from Beiersdorf Inc., S. Norwalk, CN, which is an unscented moisturizing formula for dry skin containing water, petroleum, mineral oil, mineral wax, wool wax alcohol, and 2-bromo-2-nitropropane-1.3-diol. Other viscous topical medicament carriers are "Vehicle N" (Neutrogena Corp., Los Angeles, CA), Aquaphor ointment base (Dule Laboratories, South Norwalk, CN), Unibase ointment base (Parke-Davis, Detroit, MI), and petrolatum. Other types of topical carriers are known, such as mixtures of one or more of ethanol, isopropanol, N-methylpyrollidone (NMP), and water.

It is also preferred to include into topical formulations a skin penetration agent. Many such agents are known to those of skill in the art, one of the more common being DMSO. Useful penetration agents are the class of compounds having the general formula:

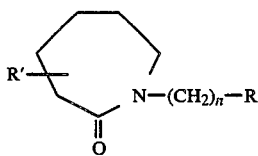

wherein R' is selected from the group consisting of H and alkyls having 1-4 carbon atoms, R is selected from the group consisting of alkyls of 1-18 carbon atoms and phenyl, and n is 0 or a positive integer from 1-10. These penetration agents are described in U.S. Pat. Nos. 3,989,816, 4,405,616, and 4,316,893, the disclosures of which are incorporated herein by reference. Examples of this class of compounds include 1-methyl-azacycloheptan-2-one, 1-octyl-azacycloheptan-2-one, and 1-nonyl-azacycloheptan-2-one. A preferred penetration enhancing agent within this class of compounds is 1-dodecyl-azacyclo- heptan-2-one, sold under the trademark Azone by Nelson Research and Development Co., Irvine, CA. Another penetration enhancer is N-methylpyrollidone (NMP), also available from Nelson Research and Development.

Topical application of the phototoxic hematoporphyrin can be enhanced by occlusion. After applying the phototoxic hematoporphyrin and the topical carrier to the afflicted skin, a barrier is placed over the area which prevents passage of the topical formulation so as to enhance absorption into the skin. An example of an occlusion barrier is Saran Wrap plastic wrap. (Dow Corporation, Midland, MI.)

While it may be necessary to apply the topical compositions of the present invention only once prior to radiation, it may also be necessary to repeat the application several times prior to exposure in order to obtain sufficient quantities of phototoxic hematoporphyrin in the afflicted tissue. For example, it may be desirable to repeat the topical administration several times over the course of one day, or several times over the course of several days. To obtain complete eradication or clearing of a particular hyperproliferative epithelial disease, it may also be necessary to repeat the entire regimen of topical or interdermal applications followed by photoactivation. Continued maintenance therapy for some disorders, such as psoriasis, may be required.

After the phototoxic hematoporphyrin has been administered to the afflicted tissue, the tissue is irradiated with an appropriate radiation source. The optimum wavelengths to achieve a phototoxic reaction with the hematoporphyrins have not been established. Activity can be seen with UVA and various parts of the visible spectrum, depending on light energy. Light sources can include, for example, a 15 watt cool white fluorescent bulb, Wood's light (UVA), a 150 watt high intensity light (white) bulb, 1600 and 5000 watt xenon arc lamps, red dye lasers, and even a slide projector with a 500 watt bulb filtered to pass light of wavelengths no longer than 600 nm. A preferred radiation source is red light (620-640 nm, corresponding to an HPD absorption band). Such wavelengths are used for the treatment of tumors because of deeper tissue penetration by the longer wavelength light.

The depth of light penetration will depend upon the light source selected. For psoriasis, where superficial lumination is desirable, long-wave UVA is desirable. At present, PUVA boxes are commonly available in all countries in the world. For cervical displasia, however, a red dye laser may be more desirable because of the ease of focusing lasers through an endoscope to the afflicted tissue. For treating cutaneous or subcutaneous disease, deeper penetration may be achieved with visible light, such as red light, particularly a laser, as noted above.

Appropriate radiation dosages can be readily determined by those of ordinary skill in the art. Light distribution in tissue is a function of incident light intensity, wavelength, optical properties of the tissue, and drug levels. Selection of the appropriate amount of radiation will be predicated upon the above factors. For example, dosage levels of red light at 370 J/cm$^2$ and UVA at 30 J/cm$^2$ have been found to give appropriate cutaneous phototoxic responses. The precise dose of radiation, within very broad limits, is not critical.

Generally, a period of time is allowed to elapse after administration of the phototoxic hematoporphyrin and before exposing the afflicted tissue to radiation. The time necessary will vary depending upon the particular disease and the mode of application, as well as other factors. In general, however, a period between about 6 hours and about 24 hours will be appropriate. This should allow sufficient time for the phototoxic hematoporphyrin to penetrate the skin and localize in the cells of the afflicted tissue.

The following examples are presented for illustrative purposes only and are not intended to limit the scope of the invention in any way. Percentages are by weight unless otherwise noted.

EXAMPLE 1

In Vitro Percutaneous Penetration Assay

The percutaneous penetration of HPD was measured in glass diffusion cells using techniques previously described. McCullough et al, (1976) *J Invest Dermatol* 66:103-107.

Hematoporphyrin Derivative was obtained in a 5 mg/ml saline solution under the trade name Photofrin from Oncology Research and Development Inc., Cheektowaga, NY. Topical formulations were prepared by lyophilizing this material in the dark, following by reconstitution in the selected vehicle. Topical carriers were obtained commercially: Azone and NMP (Nelson Research, Irvine, CA); Eucerin Cream (Beiersdorf, S. Norwalk, CN); Vehicle N (Neutrogena Corporation, Los Angles, CA); Aquaphor ointment base (Duke Laboratories, S. Norwalk, CN); Unibase ointment base (Parke-Davis, Detroit, MI); dimethylacetamide (Aldrich Chemical Corporation, Milwaukee, WI); and dimethylsulfoxide (Mallinckrodt Inc., Harris, KY).

Full-thickness skin excised from the backs of HRS/J albino hairless mice was used for these studies. HPD at a concentration of 1% in various vehicles was applied to the epidermal surface at a rate of 0.2 ml/cm$^2$. A total of 2.5-mg was applied to each diffusion cell. The dermal reservoir contained phosphate-buffered saline. Three diffusion cells were run for each vehicle. Diffusion cells were incubated with constant stirring at 28° C. HPD penetration was quantified by fluorometric analysis using an Aminco-fluoro-colorimeter equipped with Corning 5-56 excitation and 2-62 emission filters. Skin specimens were removed from the diffusion chamber upon completion of the frozen lipid nitrogen. Cryostat sections of the full-thickness skin specimens were examined for HPD fluorescence with a Nikon AFM fluorescence microscope (BV excitation and Wratten 2B barrier filters). The results are summarized below in Table I. The results in a similarly conducted study are reported in Table II.

TABLE I

Topical HPD (1%) percutaneous penetration in vitro and phototoxic activity in vivo

| Vehicle | Total penetration of HPD at 48 h° ($\mu$g/cm$^2$) |
|---|---|
| Saline | 22 ± 3 |
| Azone:isopropanol:H$_2$O (2:50:48)* | 183 ± 32 |
| Azone:ethanol:H$_2$O (2:93:5) | 127 ± 50 |
| Azone:ethanol:H$_2$O (1:94:5) | 96 ± 16 |
| Azone:ethanol:H$_2$O (0.5:94.5:5) | 48 ± 8 |
| N—methylpyrollidone:isopropanol:H$_2$O (43:30:27)* | 88 ± 48 |
| Dimethylsulfoxide:H$_2$O (80:20) | N.D. |
| Dimethylacetamide:H$_2$O (80:20) | N.D. |
| Eucerin* | N.D. |
| Vehicle N | N.D. |
| Aquaphor | N.D. |
| Unibase | N.D. |
| Petrolatum | N.D. |

*Topical 1% HPD applied in these vehicles 3 times prior to UVA irradiation (32.4 J/cm$^2$) or red light (35.2 J/cm$^2$) produced a phototoxic response in the skin.
N.D.: Experiment not done.

TABLE II

| Drug | Vehicle | Total penetration in 48 hours |
|---|---|---|
| HPD (1%) | Saline | 39 ± 6 |
| HPD (1%) | 2% Azone:93% EtOH:5% H$_2$O | 223 ± 89 |
| HPD (1%) | 1% Azone:95% EtOH:5% H$_2$O | 170 ± 28 |
| HPD (1%) | 0.5% Azone:94.5% EtOH:5% H$_2$O | 85 ± 15 |
| HPD (1%)* | 2% Azone:48% H$_2$O:50% Isoprop—OH | 325 ± 56 |
| HPD/F$_B$ (1%) | 2% Azone:48% H$_2$O:50% Isoprop—OH | 271 ± 43 |
| HPD/F$_B$ (1%) | Vehicle N | 148 ± 21 |
| HPD/F$_B$ (1%) | 43% NMP:27% H$_2$O:30% Isoprop—OH | 104 ± 19 |
| HPD (1%)* | 43% NMP:27% H$_2$O:30% Isoprop—OH | |
| HPD (1%)* | 2% Eucerin | |

*Topical formulations which produced phototoxic responses in guinea pig skin.
F$_B$: free base: prepared by acid (pH 3.5) precipitation of HPD.
NMP: N—methylpyrollidone.
Isoprop—OH: isopropyl alcohol.

The penetration of HPD was enhanced by all vehicles compared to saline. Increasing concentrations of Azone from 0.5 to 2% enhanced HPD penetration. Maximum HPD penetration was obtained with the Azone:isopropanol:H$_2$O (2:50:48) vehicle. Fluorescence microscopy of skin sections treated with HPD in this vehicle showed a more intense fluorescence in the stratum corneum, reflecting a higher concentration of HPD in that site.

EXAMPLE 2

Erythemogenic Effect of Topical Hematoporphyrin Derivative

HPD and other materials were obtained and prepared as described in Example 1.

Various topical HPD preparations or vehicle control solutions (0.1 ml) were applied to the back skin (1.5 × 1.5 cm area) one or more times before irradiation. Excess HPD was washed off the skin by mild soap and water immediately prior to irradiation. This effectively removed all HPD from the skin surface, although residual HPD in the skin was evident from the reddish color that remained after washing. Fluorescence microscopy also revealed high levels of HPD concentrated in the stratum corneum following the washing procedure. All treatments were done in duplicate in each animal. Both upper and lower back were used in these studies, with treatment and control sites localized to similar anatomic regions.

Two different light sources were used for irradiation. A red light source was provided by a modified 500 watt slide projector, filtered to pass light of wavelengths longer than 600 nm (Corning 2418 filter). The emission spectrum of the red light source was measured and the peak output found between 600 and 700 nm, delivering 9.8 mW/cm$^2$ at a distance of 10 cm from the lens. The light source, placed 10 cm above the exposure site, delivered doses of 8.8 J/cm$^2$, 17.6 J/cm$^2$ or 35.2 J/cm$^2$, representing exposure times of 15, 30, and 60 minutes, respectively. The UVA radiation source was provided by a bank of 8 UVA lamps (peak emission level 360–365 nm) contained in an HOUVA-Lite hand-foot unit (National Biological Corporation, Cleveland, OH). The light intensity measured was approximately 9 mW/cm$^2$ at a distance of 10 cm from the treatment sites, delivering doses of 8.1, 16.2, or 32.4 J/cm$^2$, representing exposure times of 15, 30, or 60 minutes. During light exposure, animals were restrained and lightly anesthetized with xylazine and ketamine.

Tables I and II indicate phototoxic formulations with an asterisk (*). The Azone:isopropanol:H$_2$O and the NMP vehicles of Table I provided significant erythema. The Eucerin vehicle of Table I also exhibited some erythema. These topical HPD formulations demonstrated erythema following irradiation with either red light or UVA. Histologic changes produced 48 to 74 hours post irradiation included mark superficial crusting, epidermal necrosis, subepidermal bullae, and a dermal inflammatory infiltrate. In contrast, the vehicle plus light or HPD without light showed no evidence of erythema and remained histologically normal. Topical HPD in either the Azone or NMP vehicle produced complete inhibition of epidermal DNA synthesis with a lesser degree of inhibition in the deeper hair roots as compared to controls.

The effect of HPD concentration in the NMP vehicle was also studied. There was a slight increase in the duration of erythema at 48 hours post irradiation with a vehicle containing 5% HPD by weight in comparison to a vehicle containing 1% HPD. Fluorescence microscopy, however, appeared to show that maximum HPD skin content is achieved with a 1% HPD/NMP formulation as compared to the 5% HPD in NMP after three applications. Three applications of HPD within a 24 hour period produced a greater degree of erythema with both the 1% and 5% formulations than did a single application administered 4 hours prior to irradiation.

EXAMPLE 3

Intradermal HPD Administration

HPD (Photofrin, Example 1) was administered intradermally in guinea pigs to selectively deliver the drug to the skin and thereby eliminate systemic exposure.

The erythemogenic effect of intradermal HPD (0.5, 5, 50, and 500 $\mu$g/cm$^2$) and irradiation with either red light or UVA, as described above, showed that doses from about 5 to about 500 $\mu$g/cm$^2$ injected 6 hours before light treatment produce significant erythema. In each case there was a dose-dependent response, with maximal erythema obtained with 500 $\mu$g per injection site. There appeared to be a more rapid onset of erythema with red light, which produced clinical effects after 24 hours post irradiation and maximal response at 48 hours. With UVA, erythema was not seen until about 48 hours after irradiation with maximal response at 72 hours.

The intradermal administration of HPD and UVA irradiation also produced an inhibition of epidermal DNA synthesis.

The extent of DNA synthesis was measured by autoradiographic techniques. At various times after light exposure, animals were injected intradermally into separate sites with 0.1 cc containing 10 $\mu$Ci of [methyl-$^3$H] thymidine (25 Ci/mmol, Amersham), [5-$^3$H-] uridine (30 Ci/mmol), and L-[4,5-$^3$H] leucine (30.7 Ci/mmol, New England Nuclear). The isotopes were administered to both areas exposed to light, as well as control areas which were not irradiated. One hour after isotope administration, the injected sites were biopsied with a 4-mm punch, fixed in Bouin's fixative for 24 hours, and prepared histologically for autoradiography. G. D. Weinstein (1965), *J Invest Dermatol* 44:413–419. The slides were coated with Kodak NTB-2 liquid nuclear track emulsion for six weeks, developed, and stained with hematotoxylin and eosin.

The labeling index was determined as a measure of DNA synthesis by counting the number of labeled basal cells per 1000 interfollicular basal cells. Epidermal RNA ($^3$H-uridine) and protein ($^3$H-leucine) synthesis was scored qualitatively on a scale of 0–3+ based on a composite of grain content and number of labeled cells. A cell was considered labeled if it contained 5 or more grains per cell. All selections were scored by two independent observers and the result averages. The autoradiographic results were expressed as percent of control:

$$\frac{\text{Labeling of } HPD + \text{light-treated sites}}{\text{Labeling of unirradiated sites}} \times (100\%)$$

Doses of 50 and 500 $\mu$g HPD produce complete inhibition of DNA synthesis at 24 hours with continued inhibition over the 72 hour observation period. A less pronounced inhibitory effect was seen with the lower doses (0.5 and 5 $\mu$g) which was accompanied by a stimulation in DNA synthesis at 48–72 hours.

EXAMPLE 4

Topical Treatment of Premalignant Tissue of the Genital Tract

Two vehicles were investigated for topical application of HPD. Vehicle number 1 consisted of Eucerin. Vehicle number 2 consisted of a mixture of NMP (43%) isopropanol (30%), and water (27%). HPD (Photofrin, Example 1) was lyophilized and then thoroughly mixed with the two respective vehicles to a final concentration of 1% or 5%.

Each topical HPD formulation was applied to DF$_1$ mice in which intraepithelial neoplasia (IN) had been induced by injection of urethane followed by 13 weeks of tetradecanol phorbol acetate treatment. Fluorescence analysis revealed a higher concentration of HPD in IN skin compared to surrounding normal skin in the mice treated with vehicle number 1. Fluorescence analysis revealed no concentration of HPD in IN compared to adjacent normal skin in animals treated with vehicle number 2. HPD concentration appeared to be related to the number of topical applications and the length of time between application and fluorescent analysis.

Three patients with premalignant lesions of the genital tract who had failed conventional attempts at control of their disease or were not considered candidates for standard therapies, were then treated by the topical application of 5% HPD in Eucerin. The topical formulation was applied to the treatment area three times a day beginning two days before radiation. Each patient, therefore, had a total of 7 topical HPD applications. The treatment area, as well as a 2.0–4.0 cm rim of surrounding clinically uninvolved tissue was exposed to the light of 630 nm provided by an argon ion pumped-dye laser (Spectro Physics 375-50). The total light dose to each treated lesion was 20–40 J/cm$^2$. The patients were studied on an out-patient basis. Follow-up examinations were performed at 24 hours, 72 hours, and weekly thereafter.

A partial response to the phototherapy after topical application of HPD was produced in one patient with vaginal intraepithelial neoplasia. The response was manifested by a transient return to normal of the vaginal Papanicolaou smear. A biopsy of the treated area 2 weeks after photoactivation showed no evidence of carcinoma in situ. Two other patients with vulvar intraepithelial neoplasia did not exhibit any response to therapy.

EXAMPLE 5

Screening HPD and Components Systemically and Locally for Cutaneous Phototoxicity A guinea pig motel was selected for studying the phototoxicity of HPD and the isolated components. HPD, DHE, hematoporphyrin and protoporphyrin were provided by Dr. Thomas J. Dougherty, Roswell Park Memorial Institute, Buffalo, NY. Hydroxyvinyldeuteroporphyrin was obtained from Porphyrin Products, Salt Lake City, UT.

Guinea pigs were treated systemically (I.P.) with the various porphyrins, each at a dose of 10 mg/kg. Animals were then irradiated with UVA (20 J/cm$^2$), either at 6 hours or 24 hours post drug administration. Erythema was graded at 24 hours post light treatment.

Treatment at 6 hours produced a significant response with HPD and DHE, with a mild response for hematoporphyrin. No response was obtained with protoporphyrin or hydroxyvinyldeuteroporphyrin. When light treatment was delayed for 24 hours, the response of HPD and DHE was greater, while mild responses were obtained with the other porphyrins. It is possible that the protoporphyrin and hydroxyvinyldeuteroporphyrin samples were contaminated with hematoporphyrin, which would account for the unexpected phototoxic effect.

In order to prevent the masking of phototoxicity by the skin irritation produced by certain topical vehicles, or false negatives due to lack of penetration of the various HPD components topically applied, the hematoporphyrins were evaluated after intradermal administration. Drugs were administered intradermally at doses ranging from 5–500 µg/0.1 ml. Sites were then treated with UVA (20 J/cm$^2$) 6 hours post drug injection. The minimum phototoxic dose of HPD and DHE was 5 µg. Hematoporphyrin required a minimum dose of 50 µg to demonstrate a phototoxic dose. Protoporphyrin and hydroxyethylvinyldeuteroporphyrin failed to exhibit phototoxicity even at doses of 500 µg. These results, therefore, are consistent with the systemic evidence.

Additional studies were done with intradermal HPD and DHE to study the drug/UVA dosimetry. Doses of UVA as low as 1 J/cm$^2$ were effective in producing erythema with DHE (5 µg/cm$^2$) with a response slightly greater than with comparable treatments with HPD. UVA treatments at 24 hours post injection, as opposed to 6 hours, produced a more pronounced erythema, with a larger area of erythema as the result of local drug diffusion from the injection site.

EXAMPLE 6

Effect of Topically Administratered DHE on Epidermal DNA Synthesis

The topical activity of DHE was evaluated in vivo in a mini-pig model.

Mini-pigs were obtained from Charles River Laboratories, Inc. (Wilmington, MA). Drug preparations were applied to small areas of dorsal skin (ca 1 inch square) according to the selected application schedules. Six hours following the last drug application, tritiated thymidine was injected into the drug treatment sites for autoradiographic assessment of epidermal proliferation as measured by epidermal labeling index. Weinstein & Van Scott, (1965) J. Invest. Derm. 44:413.

DHE was acid precipitated from a Photofrin II solution by adjusting the pH to 3.5. The precipitated DHA was washed extensively with distilled water until the pH of the filtrate reached 6.0. The DHE powder was vacuum dried, reconstituted in distilled water, and the pH adjusted to 7.0. Aqueous DHE was then mixed with isopropanol and Azone. The formulation had a final DHE concentration of 1% (w/w), and contained 48% (v/v) isopropanol, 4% (v/v) Azone, and 48% (v/v) water. This formulation was applied to selected areas of mini-pig skin approximately 6 hours before irradiation with UVA. Epidermal DNA synthesis was assayed as described above. At 0, 24, 48, and 72 hours post-irradiation, the animals were injected at the selected sites with isotopic precursors (tritiated thymidine). The animals were biopsied one hour after isotopic injection.

FIG. 1 shows the results of these studies. The data demonstrate that after 5–10 applications, topical DHE in combination with UVA produces a significant inhibition of DNA synthesis compared to the vehicle control plus UVA. The maximum effect obtained autoradiographically, and observed clinically, was at 72 hours post light treatment.

Since modifications of the above embodiments will be apparent to those skilled in the art, it is intended that this invention be limited only by the scope of the appended claims.

We claim:

1. A composition for topical application in the photochemotherapy of an epithelial disease comprising a topical carrier and a therapeutically effective amount of the component of Hematoporphyrin Derivative that is phototoxic to psoriatic tissue, said topical carrier selected from the group consisting of a cream, an ointment, a gel, a lotion and a solution containing N-methylpyrollidone or Azone.

2. The composition of claim 1 wherein said component of Hematoporphyrin Derivative is dihematoporphyrin ether.

3. The composition of claim 2 wherein the concentration of dihematoporphyrin ether is from about 0.1% to about 10% by weight.

4. The composition of claim 3 wherein the concentration of dihematoporphyrin ether is from about 0.5% to about 5% by weight.

5. The composition of claim 4 wherein the concentration of dihematoporphyrin ether is from about 0.5% to about 1.5% by weight.

6. The composition of claim 2 wherein said topical carrier contains 1-dodecyl-azacycloheptan-2-one.

7. The composition of claim 4 wherein said topical carrier contains 1-dodecyl-azacycloheptan-2-one at a concentration from about 0.5% to about 10% by weight of said composition.

8. The composition of claim 7 wherein said concentration of 1-dodecyl-azacycloheptan-2-one is from about 3% to about 5% by weight of said composition.

9. The composition of claim 5 wherein said topical carrier contains from about 3% to about 5% 1-dodecyl-azacycloheptan-2-one by weight of said composition.

10. The composition of claim 2 wherein said topical carrier is a viscous topical medicament carrier.

11. The composition of claim 3 wherein said topical carrier is a viscous topical medicament carrier.

12. The composition of claim 4 wherein said topical carrier is a viscous topical medicament carrier.

13. The composition of claim 5 wherein said topical carrier is a viscous topical medicament carrier.

14. The composition of claim 7 wherein said topical carrier is a viscous topical medicament carrier.

15. A composition for topical application in the photochemotherapy of hyperproliferative epithelial disease comprising a topical carrier and a therapeutically effective amount of Hematoporphyrin Derivative, said topical carrier selected from the group consisting of a cream, an ointment, a gel, a lotion and a solution containing N-methylpyrollidone or Azone.

16. The composition of claim 15 wherein the concentration of Hematoporphyrin Derivative is from about 0.1% to about 10% by weight.

17. The composition of claim 16 wherein the concentration of Hematoporphyrin Derivative is from about 0.5% to about 5% by weight.

18. The composition of claim 17 wherein the concentration of Hematoporphyrin Derivative is from about 0.5% to about 1.5% by weight.

19. The composition of claim 15 wherein said topical carrier contains 1-dodecyl-azacycloheptan-2-one.

20. The composition of claim 16 wherein said topical carrier contains 1-dodecyl-azacycloheptan-2-one.

21. The composition of claim 15 wherein said topical carrier is a viscous topical medicament carrier.

22. The composition of claim 16 wherein said topical carrier is a viscous topical medicament carrier.

23. The composition of claim 19 wherein said topical carrier is a viscous topical medicament carrier.

24. A method of photochemotherapy for hyperproliferative epithelial diseases comprising:
    (a) treating an area of tissue afflicted by a proliferative epithelial disease by applying topically or intradermally a therapeutically effective amount of Hematoporphyrin Derivative or the component of Hematoporphyrin Derivative that is phototoxic to psoriatic tissue; and
    (b) exposing said treated tissue to radiation that photoactivates said component of Hematoporphyrin Derivative to produce a cytotoxic response in said afflicted tissue.

25. The method of claim 24 wherein step (a) comprises treating said afflicted tissue with dihematoporphyrin ether.

26. The method of claim 24 wherein step (a) comprises treating said afflicted tissue with Hematoporphyrin Derivative.

27. The method of claim 25 wherein said radiation is selected from the group consisting of the visible spectrum and the ultraviolet spectrum.

28. The method of claim 25 wherein said radiation is selected from the group consisting of red light and UVA.

29. The method of claim 25 wherein said dihematoporphyrin ether is applied to said afflicted tissue topically in a composition comprising a viscous topical medicament carrier.

30. The method of claim 29 wherein the concentration of dihematoporphyrin ether in said composition is from about 0.1% to about 10% by weight.

31. The method of claim 29 wherein the concentration of dihematoporphyrin ether in said composition is from about 0.5% to about 5% by weight.

32. The method of claim 25 wherein said dihematoporphyrin ether is applied topically in the presence of a skin penetration enhancing agent.

33. The method of claim 32 wherein said skin penetration enhancing agent is 1-dodecyl-azacycloheptan-2-one.

34. The method of claim 29 wherein said topical carrier comprises a skin penetration enhancing agent.

35. The method of claim 29 wherein said composition further comprises 1-dodecyl-azacycloheptan-2-one.

36. The method of claim 31 wherein said composition further comprises from about 1% to about 4% 1-dodecyl-azacycloheptan-2-one by weight.

37. The method of claim 24 wherein said hyperproliferative epithelial disease is selected from the group consisting of psoriasis and cervical displasia.

38. The method of claim 27 wherein said hyperproliferative epithelial disease is selected from the group consisting of psoriasis and cervical displasia.

39. The method of claim 31 wherein said hyperproliferative epithelial disease is selected from the group consisting of psoriasis and cervical displasia.

40. The method of claim 35 wherein said hyperproliferative epithelial disease is selected from the group consisting of psoriasis and cervical displasia.

41. The method of claim 24 wherein said component of Hematoporphyrin Derivative is applied topically.

42. The method claim 41 wherein said component of Hematoporphyrin Derivative is dihematoporphyrin ether.

43. The method of claim 41 wherein Hematoporphyrin Derivative is applied topically.

44. The method of claim 41 wherein said hyperproliferative epithelial disease is selected from the group consisting of psoriasis and cervical dysplasia.

* * * * *